(12) United States Patent
Vincent et al.

(10) Patent No.: US 11,621,084 B2
(45) Date of Patent: Apr. 4, 2023

(54) IMAGE PROCESSING METHOD

(71) Applicant: Mako Surgical Corp., Weston, FL (US)

(72) Inventors: Graham Richard Vincent, Manchester (GB); Michael Antony Bowes, Derbyshire (GB); Kevin De Souza, West Yorkshire (GB)

(73) Assignee: Mako Surgical Corp., Ft, Lauderdale, FL (US)

( * ) Notice: Subject to any disclaimer, the term of this patent is extended or adjusted under 35 U.S.C. 154(b) by 751 days.

(21) Appl. No.: 15/776,235

(22) PCT Filed: Nov. 16, 2016

(86) PCT No.: PCT/GB2016/053574
§ 371 (c)(1),
(2) Date: May 15, 2018

(87) PCT Pub. No.: WO2017/085478
PCT Pub. Date: May 26, 2017

(65) Prior Publication Data
US 2020/0126656 A1    Apr. 23, 2020

(30) Foreign Application Priority Data
Nov. 20, 2015    (GB) ..................... 1520467

(51) Int. Cl.
*G16H 50/50* (2018.01)
*G16H 30/40* (2018.01)

(52) U.S. Cl.
CPC ............. *G16H 50/50* (2018.01); *G16H 30/40* (2018.01)

(58) Field of Classification Search
CPC ........ G16H 50/50; G16H 30/40; G16H 70/60; G16H 10/60; A61F 2/30942; A61F 2002/30948
See application file for complete search history.

(56) References Cited

U.S. PATENT DOCUMENTS 6,161,080 A * 12/2000 Aouni-Ateshian .... G16H 50/50
703/11
8,521,492 B2 * 8/2013 Otto ....................... G16H 20/40
703/6

(Continued)

FOREIGN PATENT DOCUMENTS

WO    2006087190 A1    8/2006
WO    2015110282 A1    7/2015

OTHER PUBLICATIONS

D. van den Heever, C. Scheffer, P. Erasmus and E. Dillon, "Development and testing of patient-specific knee replacements," 2012 Annual International Conference of the IEEE Engineering in Medicine and Biology Society, 2012, pp. 4875-4878, doi: 10.1109/EMBC.2012.6347086. (Year: 2012).*

(Continued)

*Primary Examiner* — Evangeline Barr
(74) *Attorney, Agent, or Firm* — Lerner, David, Littenberg, Krumholz & Mentlik, LLP

(57) ABSTRACT

A computer-implemented method for generating anatomical data associated with a musculoskeletal joint, the method comprising: receiving as input variation data representing change with time of a musculoskeletal joint of interest caused by a condition; receiving as input patient data representing the musculoskeletal joint of interest of a patient at a current time; and processing the variation data and the patient data to generate said anatomical data, wherein said anatomical data comprises data indicating the musculoskel- (Continued)

etal joint of interest of the patient at a predetermined time different to the current time.

10 Claims, 5 Drawing Sheets

(56) References Cited

U.S. PATENT DOCUMENTS

| | | | |
|---|---|---|---|
| 2006/0002600 A1* | 1/2006 | Martel-Pelletier | G06T 7/0012 382/128 |
| 2006/0216681 A1* | 9/2006 | Walker | G06T 7/74 434/274 |
| 2011/0112808 A1* | 5/2011 | Anderson | G16H 50/50 703/2 |
| 2011/0257507 A1 | 10/2011 | Gregory et al. | |
| 2014/0257508 A1* | 9/2014 | Bojarski | A61F 2/30942 703/1 |
| 2014/0371897 A1* | 12/2014 | Lin | G05B 19/4099 700/118 |

OTHER PUBLICATIONS

International Search Report for PCT Application PCT/GB2016/053574 dated Mar. 17, 2017.
Search Report for Application No. GB1520467.0 dated Apr. 18, 2016.

* cited by examiner

○ Male Non-OA
▫ Male KL 2
▪ Male KL 3-4
○ Female Non-OA
· Female KL 2
● Female KL 3-4

IMAGE PROCESSING METHOD

CROSS-REFERENCE TO RELATED APPLICATIONS

The present application is a national phase entry under 35 U.S.C. § 371 of International Application No. PCT/GB2016/053574 filed Nov. 16, 2016, published in English, which claims priority from Great Britain Application No. 1520467.0 filed on Nov. 20, 2015 all of which are incorporated herein by reference.

BACKGROUND OF THE DISCLOSURE

The present invention relates to methods and apparatus for generating anatomical data associated with a musculoskeletal joint.

Osteoarthritis ("OA") is a degenerative joint disease in which joints degrade with time causing joint pain and difficulties with mobility. With ageing populations osteoarthritis has become common place, with around 8 million people in the UK and around 27 million people in the US suffering from osteoarthritis.

The causes of OA are not well understood, however a number of factors are known to contribute to likelihood of disease onset in certain joints such as the knee. Such factors include high body mass index, traumatic damage to ligaments and menisci, valgus alignment of the knees, and the way in which the joint is used in daily activities.

Knee osteoarthritis involves all of the tissues in the knee, including bone, cartilage, menisci, ligaments, capsule and synovial tissue. Individual patients may have damage to some or all of these tissues, and at a particular point in time, each patient knee may contain any combination of damaged tissues. Diagnosis typically is by radiographic scoring of bone change (osteophytes and bone damage) and joint space narrowing (indicating that cartilage has been lost from the surfaces of articulating bone). Osteophytes grow around the cartilage plate of each bone in the knee, and similarly are usually considered to be unstructured and random in their development over time and diagnosis typically takes severity osteophytes into account.

Due to the wide range of tissues involved, and the various factors known to contribute to likelihood of disease, OA is widely considered to be heterogeneous in terms of the trajectory of tissue damage for each individual.

Neogi et. al. "Magnetic Resonance Imaging-Based Three-Dimensional Bone Shape of the Knee Predicts Onset of Knee Osteoarthritis" examined whether it is possible to predict the onset of radiographic knee osteoarthritis, concluding that characteristic features of 3-D bone shape can be used to predict later onset of radiographic osteoarthritis. The work of Neogi et. al. considered differences between a population with OA and a population without OA and considers whether general characteristic differences of bone shape between the two populations as a whole can be used as a predictor of future development of osteoarthritis.

Various medical and surgical interventions for osteoarthritis exist. For example, modern orthopaedic surgery allows routine surgical repair of joints, sometimes referred to as arthroplasty. Arthroplasty may involve reshaping of a joint by modifying an existing joint surface and bone to provide a joint that operates more effectively. In recent decades surgical replacement of joints or joint surfaces with a prosthesis has been the most common and successful form of arthroplasty and has become a common treatment for osteoarthritis. Prostheses for a particular joint typically are based upon a standard shape of a joint. Some account for variation amongst patients is typically provided by prostheses for a particular joint being available in a range of sizes, with a most appropriate size being selected to fit a patient. United States Patent Publication Number US2008/058947 also describes a set of distal femoral knee prostheses that are designed to more closely correspond to the physical anatomy of female patients.

There remains, however, a need for improvements in providing medical and surgical interventions for musculoskeletal joints.

BRIEF SUMMARY

According to a first aspect of the invention there is provided a computer-implemented method for generating anatomical data associated with a musculoskeletal joint, the method comprising: receiving as input variation data representing change with time of a musculoskeletal joint of interest caused by a condition; receiving as input patient data representing the musculoskeletal join of interest of a patient at a current time; processing the variation data and the patient data to generate said anatomical data, wherein said anatomical data comprises data indicating the musculoskeletal joint of interest of the patient at a predetermined time different to the current time.

As described above, a large number of factors that vary significantly between individuals are understood to contribute to development of musculoskeletal joints including body mass index, traumatic damage to ligaments and menisci, valgus alignment of the knees, and the way in which the joint is used in daily activities. The inventors have surprisingly realized that it is possible that variation with time of a condition can be characterized and the characteristic variation with time can be used to generate anatomical data for a musculoskeletal joint of interest of a patient that provides an indication of the musculoskeletal joint of interest of the patient in a future or past condition. In particular, the inventors have realized that the most significant factor affecting shape of a joint of a patient with osteoarthritis is the osteoarthritis itself, rather than other factors that may vary significantly between individuals, and a general characteristic variation derived from a population can provide an accurate indication of variation for a particular patient of the population.

The anatomical data may be used to provide a medical intervention. For example determining an indication of the musculoskeletal joint of interest of the patient in a past condition allows surgical intervention that is tailored to the patient based upon the patient's joint itself. For example, a surgical plan suitable for guiding a surgeon, or for guiding automated surgical equipment, may be generated based upon the anatomical data. The surgical plan may, for example, provide data indicating how a joint should be modified by a surgical procedure to return the joint to a non-diseased state. Alternatively, the anatomical data may be used to generate a customized prosthesis for the patient based upon their own joint, but with effects of disease removed.

The anatomical data may additionally or alternatively be used for non-surgical interventions such as for analysis of efficacy of drugs, physiotherapy or any other medical intervention that may be used to mitigate a condition. The condition may be osteoarthritis. The anatomical data may comprise data suitable for generation of a prosthesis for the musculoskeletal joint of interest of the patient.

The variation data may comprise an indication of variation with time of the shape of the musculoskeletal joint of interest caused by the condition. The variation data may be associated with a training set of data associated with individuals other than the patient.

The patient data representing the musculoskeletal joint of interest may comprise a representation of the shape of the musculoskeletal joint of interest of the patient.

The representation of the shape of the musculoskeletal joint of interest of the patient may be based upon a parameterisation of the musculoskeletal joint of interest. The method may further comprise generating the patient data by: receiving image data obtained from the patient; and processing the image data to generate the parameterisation.

The representation of the shape of the musculoskeletal joint of interest may comprise a plurality of principal components of the shape of the musculoskeletal joint of interest. Processing the variation data and the patient data to generate said anatomical data may comprise varying the shape represented by the patient data based upon the variation data. The variation data may comprise a vector. Varying the shape represented by the patient data based upon the variation data may comprise applying the vector to the parameterisation. Applying the vector to the parameterisation may comprise: determining a relationship between the patient data and an average shape; and varying the shape represented by the patient data based upon the determined relationship. The average shape may be an average shape obtained from patients in the absence of osteoarthritis.

The anatomical region of interest may be a joint of the body selected from the group consisting of: a hip joint; and a knee joint. The anatomical data may comprise a representation of the anatomical region of interest with reduced effects of the condition. The method may further comprise manufacturing a prosthesis for the patient based upon the anatomical data. The method may further comprise generating the variation data. Generating the variation data may comprise determining an average change with time of a plurality of musculoskeletal joints of interest. The anatomical data may comprise data suitable for providing a medical intervention for the musculoskeletal joint of interest of the patient.

According to a second aspect of the invention there is provided a method for generating prosthesis data, the method comprising: receiving as input variation data representing change of an anatomical region of interest caused by a condition; receiving as input patient data representing the anatomical region of interest of a patient; and processing the variation data and the patient data to generate said prosthesis data, said prosthesis data being suitable for generation of a prosthesis for the anatomical region of interest of the patient. Aspects of the invention may be combined. For example, features described above in the context of the first aspect may also be used in the context of the second embodiment.

Aspects of the invention can be implemented in any convenient form. For example computer programs may be provided to carry out the methods described herein. Such computer programs may be carried on appropriate computer readable media which term includes appropriate tangible storage devices (e.g. discs). Aspects of the invention can also be implemented by way of appropriately programmed computers.

BRIEF DESCRIPTION OF THE DRAWINGS

Embodiments of the present invention will now be described, by way of example only, with reference to the accompanying drawings, in which.

DETAILED DESCRIPTION

Figure 1:
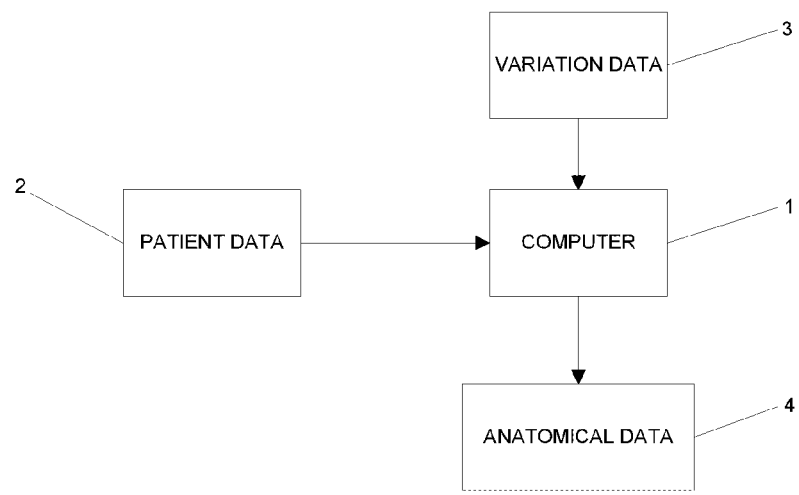
FIG. 1 is a schematic illustration of a system for generating anatomical data indicating a musculoskeletal joint of interest of a patient.

Referring to FIG. 1, a computer 1 is arranged to receive patient data 2 associated with an anatomical region of interest comprising a musculoskeletal joint of interest of a patient in a diseased state. The patient data 2 is associated with a parameterisation of the anatomical region of interest of the patient generated based upon three-dimensional image data in which features of the anatomical region of interest have been identified. For example, the three-dimensional image data may be X-ray computed tomography image data and the parameterisation may be generated by fitting to the three-dimensional image data a statistical model such as an active appearance model or active shape model, which has been created based upon a training set of images of anatomical regions of interest of the same type as the anatomical region of interest that is the subject of patient data 2. The model may be any statistical model of the variation within the training images. The statistical model may for example be generated by processing the training set of images to generate a mean model and a range of variation from the mean model of the training set. The parameterisation indicates features of the anatomical region of interest represented in the image data and can therefore be used to identify features of the represented anatomical region of interest. A suitable model fitting technique is described in International Patent Publication No. WO2011/098752, the contents of which are hereby incorporated by reference.

The computer 1 is further arranged to receive variation data 3. The variation data 3 is data associated with variation of the anatomical region of interest over time in the presence of osteoarthritis and may be generated based upon analysis of anatomical regions of interest of patients with osteoarthritis over time, as described in further detail below. The inventors have realized that change of the anatomical region of interest in the presence of osteoarthritis follows a typical pattern and analysis of patient data indicating change of an anatomical area of interest in patients can be used to generate an indication of historical change for patients, for example where data indicating change of the anatomical area of interest in patients is not available, as is typically the case, or may be used to predict future change of the anatomical area of interest.

The patient data 2 is processed based upon the variation data 3 to generate anatomical data 4. The anatomical data 4 provides an indication of the musculoskeletal joint of interest at a predetermined time that is different to the time at which the patient data 2 is obtained from the patient, and may be a previous state or a future state of the joint. The anatomical data may, for example, provide a model from which a prosthesis for the anatomical region of interest can be generated that is customized for the patient.

For example, the patient data 2 may be three-dimensional image data of a knee of a patient that has been affected by osteoarthritis and the variation data 3 may be data indicating variation of a knee of a patient that has osteoarthritis and the anatomical data 4 may provide a model of the knee of the patient that represents the knee of the patient in a state without at least some of the effects of osteoarthritis, or that represents the knee with further effects of osteoarthritis.

The anatomical data may be used to provide a medical intervention. For example determining an indication of the musculoskeletal joint of interest of the patient in a past condition allows surgical intervention that is tailored to the patient based upon the patient's joint itself. For example, a surgical plan suitable for guiding a surgeon, or for guiding automated surgical equipment, may be generated based upon the anatomical data. The surgical plan may, for example, provide data indicating how a joint should be modified by a surgical procedure to return the joint to a non-diseased state. Alternatively, the anatomical data may be used to generate a customized prosthesis for the patient based upon their own joint, but with effects of disease removed.

The anatomical data may additionally or alternatively be used for non-surgical interventions such as for analysis of efficacy of drugs, physiotherapy or any other medical intervention that may be used to mitigate a condition. Analysis of efficacy of a non-surgical intervention may be performed, for example, by generating predicted anatomical data indicating a future state of a joint without intervention and comparing data of the joint following medical intervention with the generated anatomical data to determine whether the intervention caused the joint to change in a way that is different to the predicted anatomical data.

Figure 2:
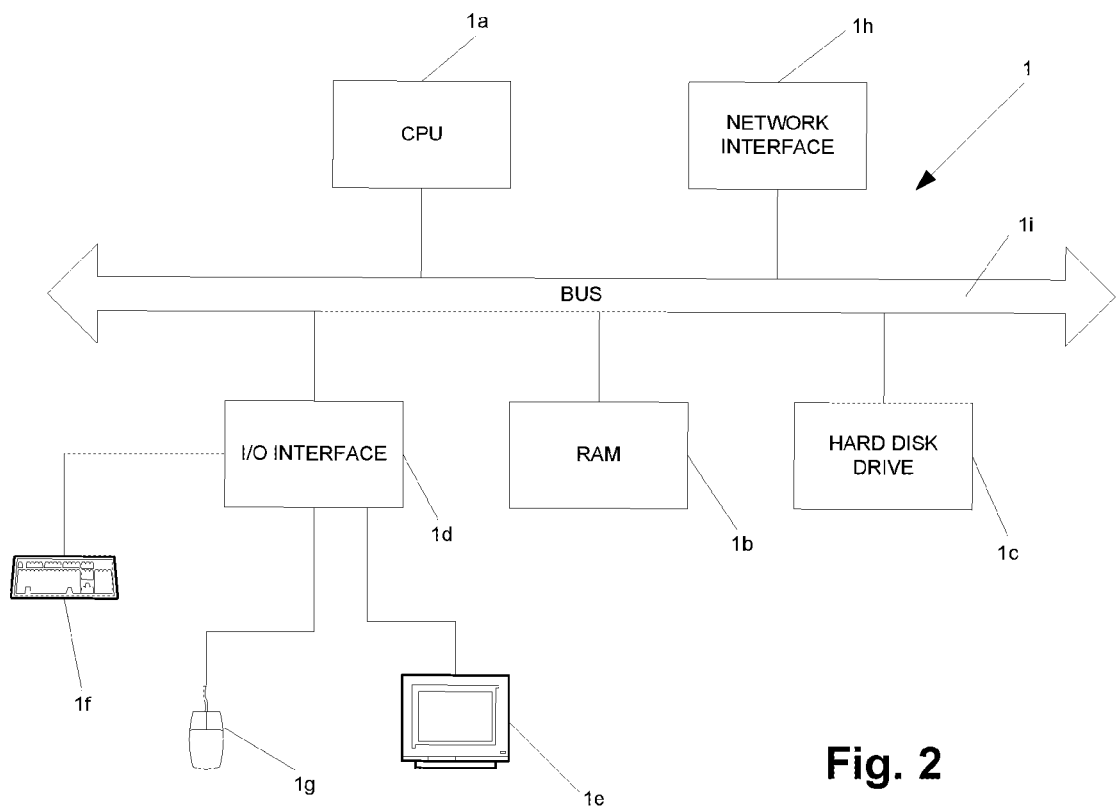
FIG. 2 is a schematic illustration showing a computer of the imaging arrangement of FIG. 1.

FIG. 2 shows the computer 1 in further detail. It can be seen that the computer comprises a CPU 1a which is configured to read and execute instructions stored in a volatile memory 1b which takes the form of a random access memory. The volatile memory 1b stores instructions for execution by the CPU 1a and data used by those instructions. For example, in use, the variation data 3 and patient data 2 FIG. 1 may be stored in the volatile memory 1b.

The computer 1 further comprises non-volatile storage in the form of a hard disc drive 1c. The data generated by the variation data 3 and the patient data 2 may be stored on the hard disc drive 1c. The computer 1 further comprises an I/O interface 1d to which is connected peripheral devices used in connection with the computer 1. More particularly, a display 1e is configured so as to display output from the computer 1. The display 1e may, for example, display a representation of the patient data 2 and anatomical data 4. Input devices are also connected to the I/O interface 1d. Such input devices may include a keyboard 1f and a mouse 1g which allow user interaction with the computer 1. A network interface 1h allows the computer 1 to be connected to an appropriate computer network so as to receive and transmit data from and to other computing devices. The CPU 1a, volatile memory 1b, hard disc drive 1c, I/O interface 1d, and network interface 1h, are connected together by a bus 1i.

Figure 3:
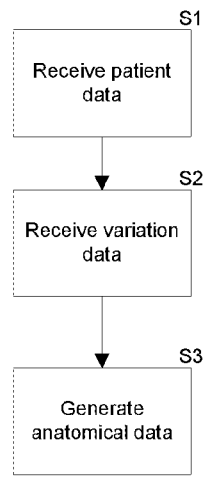
FIG. 3 is a flowchart showing processing to generate anatomical data indicating a musculoskeletal joint of interest of a patient.

FIG. 3 shows processing carried out to generate the anatomical data 4. At step S1 of FIG. 3 patient data is received. As indicated above the patient data is associated with a parameterisation of an anatomical region of interest of a patient in a diseased state. At step S2 variation data is received. The variation data is associated with variation of the anatomical region of interest over time in the presence of osteoarthritis. At step S3 the patient data and the variation data are processed to generate anatomical data associated with the anatomical region of interest of the patient.

The variation data allows change of the anatomical region of interest in the presence of osteoarthritis over time to be modelled such that change caused by osteoarthritis with time can be simulated by varying the shape of the anatomical region of interest of the patient as indicated by the variation data. The anatomical data therefore can be used to model the anatomical region of interest in the absence of the effects of osteoarthritis, or to model the anatomical region of interest in the presence of further effects of osteoarthritis. The anatomical data can therefore be used to provide a medical intervention, for example by generating a customized prosthesis of the anatomical region of interest that is based upon the patient's own anatomy with effects of osteoarthritis removed.

Figure 4:
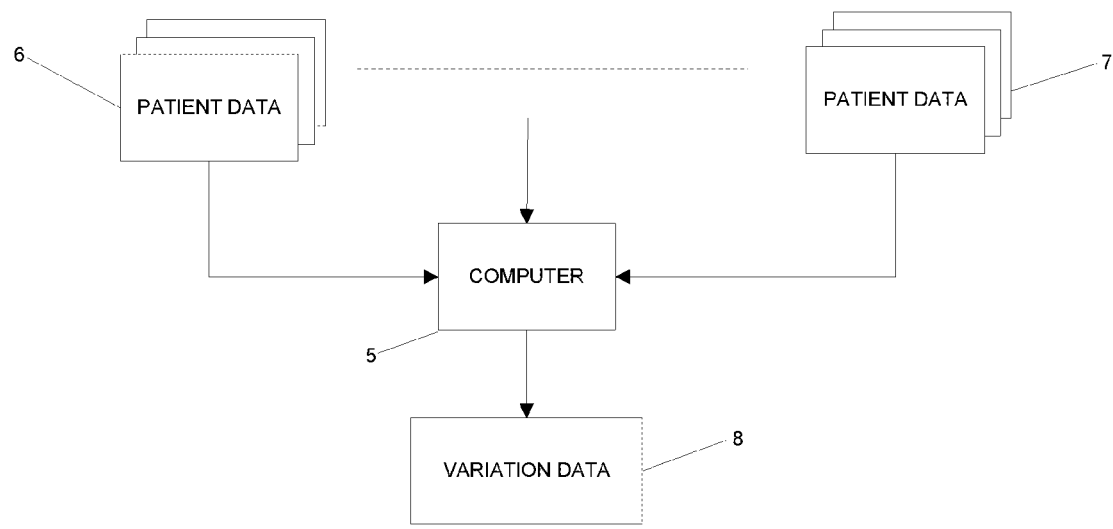
FIG. 4 is a schematic illustration of a system for generating variation data suitable for use in the processing of FIG. 3.

As indicated above, the variation data is associated with variation of the anatomical region of interest over time in the presence of osteoarthritis. The variation data may for example be generated by analysis of a training set of images of the anatomical region of interest obtained from patients with osteoarthritis over a period of time. FIG. 4 shows a schematic illustration of a system for generation of variation data suitable for use in the processing of FIG. 3. As shown in FIG. 4, a computer 5 is arranged to receive data associated with a plurality of patients, of which data 6, 7 associated with two patients is shown. Each of the patients associated with data 6, 7 has the same disease associated with the patient for which prosthetic data is to be generated using the processing of FIG. 3.

Each of data 6, 7 comprises a plurality of images of the anatomical region of interest obtained from the respective patient at a plurality of different times over a time period. For example, data 6 may comprise ten images, with each of the ten images having been obtained from a first patient at year intervals over ten years during the development of osteoarthritis and data 7 may comprise a corresponding ten images obtained from a second patient at the same intervals. The computer 5 processes the received patient data to generate variation data 8 indicating variation of the anatomical area of interest with time in the presence of disease. Processing the received patient data to generate variation data will now be described with reference to FIG. 5.

Figure 5:
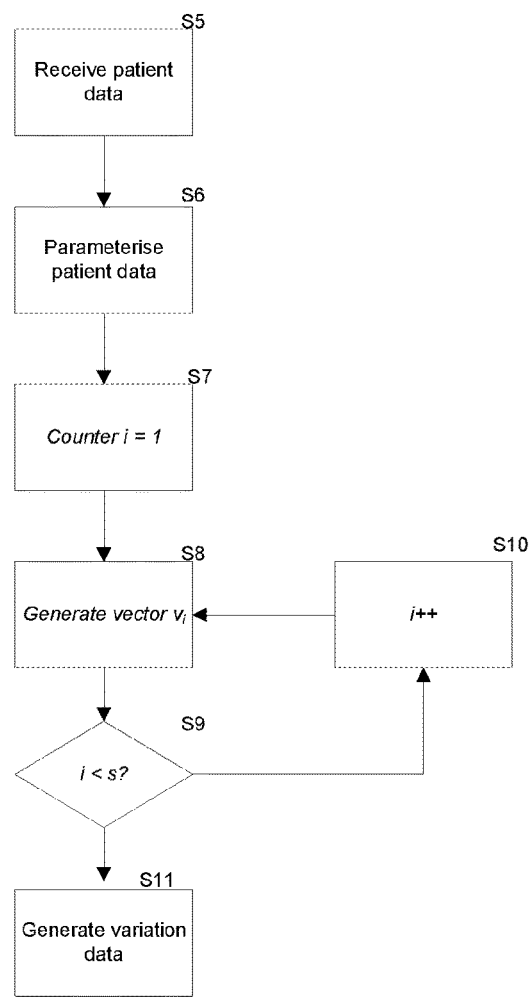
FIG. 5 is a flowchart showing processing to generate the variation data suitable for use in the processing of FIG. 3.

At step S5 of FIG. 5 patient data is received. As indicated above, the patient data comprises r images ap1, . . . , apr for each patient p, p∈{1, . . . , s}, with each image api being associated with a time i in a time period during which the patient is monitored and during which the anatomical region of interest changed as a result of osteoarthritis. Each set of r images associated with a patient p therefore provides an indication of change of the anatomical region of interest for the patient p over time. At step S6 each image of the patient data is parameterised to identify features of the imaged anatomical region of interest. The parameterisation is performed in a corresponding manner to the parameterisation of the patient data received at step S1 of FIG. 3.

The parameterisation generated at step S6 parameterises a common set of features of the anatomical region of interest into a vector space. It will be appreciated that any suitable parameterisation can be used. For example, each parameterisation can have a parameter for the x, y and z values of each of a set of anatomical 3D points which describe the anatomical region of interest and are anatomically corresponded i.e. in the same anatomical places on each image. Alternatively, the parameterisation can be a low dimension representation of the x, y and z values of each of a set of anatomical 3D points, generated by standard dimensionality reduction methods such as principal component analysis. Whichever parameterisation process is used, the parameterisation provides an instance of anatomically corresponded anatomical data, for example the shapes of the bony anatomy as in FIG. 6.

At step S7 a counter i is initialized to a value 1 and at step S8 the parameterised patient data for patient i is processed to generate a vector vi indicating change of the anatomical region of interest of the patient i over time. For example, the vector vi may be generated using regression analysis of the parameterisation associated with each image ap1, . . . , apr plotted against time associated with each image. For example, each parameterisation may be a point in a vector space having a dimension associated with each x, y and z values of each in a set of anatomical points and a further dimension associated with time and the vector indicating change of the anatomical region of interest of each patient may comprise a best fit vector through the parameterisation for the patient. It will be appreciated however that such a parameterisation typically comprises a large number of points. For example, a typical parameterisation of the head of a femur comprises of the order of 30000 points and as such a vector having a dimension for each point of the parameterisation may be computationally expensive to generate and process. As such the parameterisation for each image may be processed to form a new parameterisation using principal components analysis to determine a plurality of principal components and the vector may be indicative of change of the principal components over time. A typical number of principal components has been found to be 70 such that the vector vi for each patient may be a vector having 70 dimensions.

Given the way in which osteoarthritis develops it has been found that the direction associated with the vector vi provides movement in the time direction that is linear within a population. Additionally, it has been found that the direction of the vector in shape space has sufficient correspondence within a population that a vector generated from data obtained from a population can be used to meaningfully predict variation of an individual.

It has been found that osteoarthritis develops in a predictable way in the majority of the population, however minority populations, such as those with excess valgus angle at the knee ("knock-kneed") also progress in a linear fashion, but in a different direction in shape space such that variation data may be required to be selected for some individuals based upon a predetermined characteristic of the individual. As such, in some embodiments pre-processing is performed to select variation data for a patient based upon a characteristic of the patient, the variation data being selected from a set of possible variation data, each of the variation data having an associated characteristic. For example, each patient for which training images are received at step S5 may share a property or a plurality of properties with the patient for which the variation data is to be used. In this way, variation data that is customized for the use in generation of anatomical data for particular patients may be generated.

At step S9 a check is performed to determine whether the value of the counter i is less than the number of patients s. If it is determined that i is less than s then more patients remain to be processed and at step S10 the counter i is incremented and the processing of step S8 is repeated for the next patient. If it is determined at step S11 that the data for each patient p has been processed then at step S11 the vectors vp are processed to generate variation data v indicating average change for the patients p. The variation data v may for example be a vector indicating average change over all patients and may be generated in any convenient way, for example using regression analysis to determine a vector that best fits the plurality of vectors vp.

As described above, change caused by osteoarthritis can be simulated by varying the shape of the anatomical region of interest of the patient as indicated by the variation data. The vector v provides an indication of average variation of the shape of the anatomical region of interest with time in the presence of osteoarthritis. It has surprisingly been found that the average variation indicated by the vector v can be applied to the shape of the patient data to generate anatomical data that provides a strong correlation with actual change of the shape of anatomical region of interest of the patient. Whilst it has previously been shown that a population of patients with osteoarthritis have a characteristic shape that can be used to predict whether a patient may develop osteoarthritis, the realization that the characteristic shape can be determined from a population and subsequently applied to individual patients to provide data that can be used in medical interventions is a surprising result.

Figure 6:
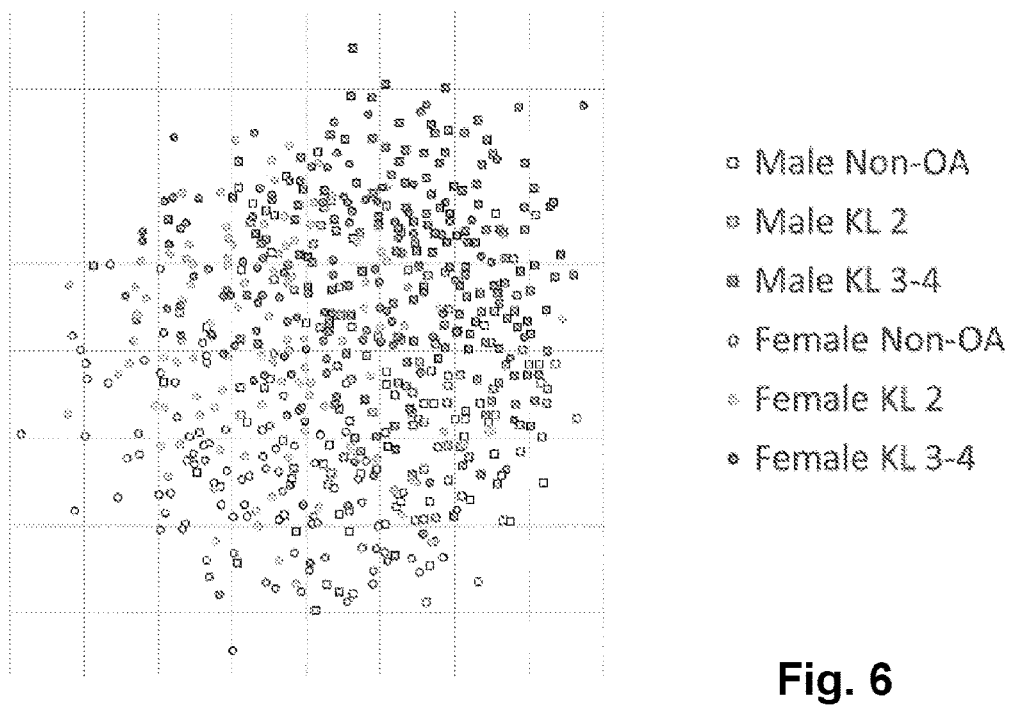
FIG. 6 is a Sammon plot illustrating distribution of shape of femurs in male and female populations with and without osteoarthritis.

FIG. 6, shows shape distribution of all 9,437 knees from volunteers aged 45-70 who entered the Osteoarthritis Initiative. All knees were fitted and parameterised with the shape model described above. The figure, which is a Sammon plot reducing the parameterisations to 2 dimensions, was decimated for display purposes by removing shapes which were close in shape space, so as to leave 600 knees. The figure shows the 95% confidence ellipse for males and females with and without OA. It can be seen that the presence of OA contributes significantly to the variability in shape and demonstrates the characteristic shape of osteoarthritis.

Figure 7:
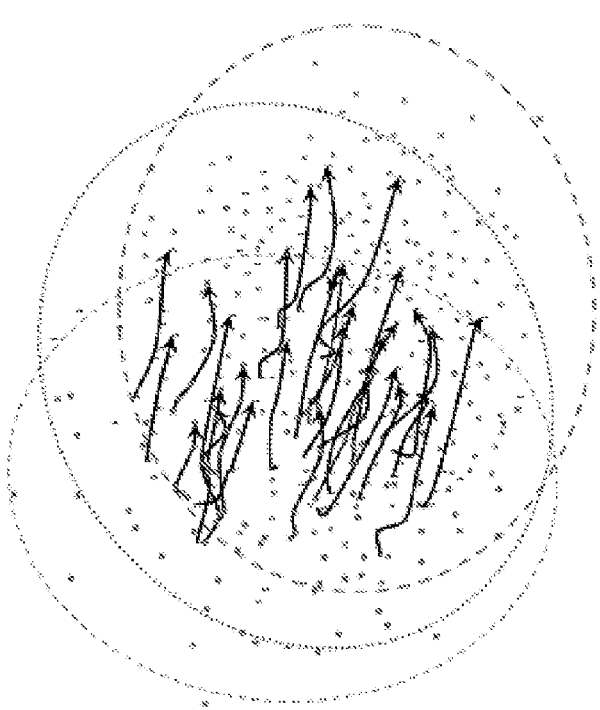
FIG. 7 is a Sammon plot illustrating change of shape of femurs of a number of individuals.

FIG. 7 shows a Sammon plot of change in shape of a set of individuals with osteoarthritis. As can be seen from FIG. 7, the change of shape of all of the individuals in two dimensions has a high correspondence, indicating that change in shape for all individuals generally follows the same characteristic direction.

In order to generate anatomical data from a current parameterisation P associated with an anatomical region of interest of a patient, the vector $-\alpha \overline{u}$ may be applied to the parameterisation P to generate a new parameterisation P' where $\overline{u}$ is the unit vector indicating the variation in the presence of osteoarthritis, and the scalar value $\alpha$ limits the allowed distance along the vector, where $\alpha$ can be estimated in a number of ways. In one embodiment consider the infinite line L in parameter space containing P and parallel to $\overline{u}$. Define M as the projection of the parameterisation of the mean non-osteoarthritis shape onto L. M indicates the closest shape to the mean non-osteoarthritis shape consistent with P and allowable on the subspace represented by osteoarthritis variation. The estimate of $\alpha$ is then limited by the Euclidean distance between M and P (i.e. $\alpha < \|M-P\|$). In an alternative embodiment, a graphical user interface can be used to visualize the change and $\alpha$ determined by a surgeon who has to balance an ideal non-osteoarthritis outcome with practical surgical and anatomical constraints.

The variation data v generated at step S11 provides the variation data 3 of FIG. 1 and can be processed as described above with reference to FIG. 3 to generate anatomical data. As described above, the anatomical data provides a representation of the anatomical region of interest in a state at a time that is different to the time at which the patient data is obtained from the patient, provides a model from which a prosthesis for the anatomical region of interest can be generated that is customized for the patient. The prosthetic data may be processed in any convenient way to generate the prosthesis, for example using known three-dimensional printing techniques.

Figure 8A:
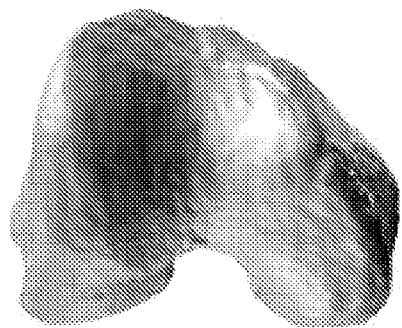
FIGS. 8A to 8C graphically represent actual and predicted change of shape of a femur of a patient.
Figure 8B:
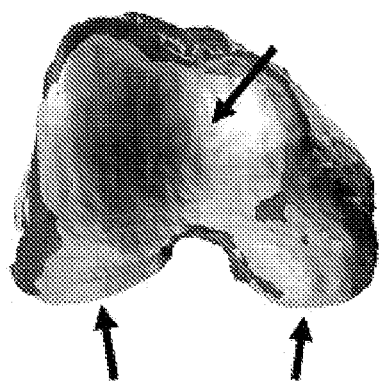
Figure 8C:
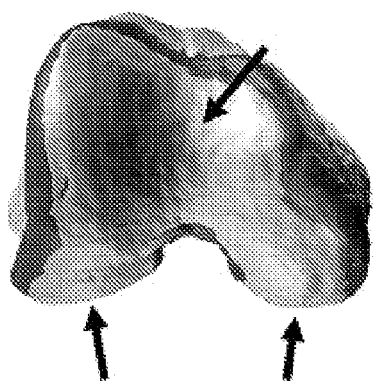

FIGS. 8A to 8C illustrate the ability to predict change of shape of a femur using the methods described above. FIG. 8A shows a femur of an individual before any effects of osteoarthritis and FIG. 8B shows actual shape of the femur of the individual after eight years. In FIG. 8B dark shaded area illustrates areas in which bony material has increased relative to FIG. 8A. Areas indicated by arrows can be seen to include shrinkage and flattening relative to FIG. 8B that is also caused by osteoarthritis. FIG. 8C shows predicted shape of the femur based upon the shape of FIG. 8A but modified using variation data generated as described above based upon a population of sample shapes. It can be seen that the predicted shape of FIG. 8C includes a dark shaded area indicating areas in which bony material has increased that corresponds closely to the dark shaded area of FIG. 8B. Additionally, arrows in FIG. 8C indicate areas that include shrinkage and flattening that also correspond to the areas of shrinkage and flattening in FIG. 8B. As can be seen from FIGS. 8A to 8C, predicted shape change shown in FIG. 8C for an individual using variation data generated from a general population of an individual closely matches actual shape change as shown in FIG. 8B.

The anatomical region of interest may be any musculoskeletal joint of interest that is affected by disease. For example the anatomical region of interest may be a knee joint including the femur, tibia and patella or a hip joint including the femur and acetabulum of the pelvis.

Whilst it has been described in the above that the change is caused by osteoarthritis it will be appreciated that the methods described above can be used to generate anatomical data representing a musculoskeletal joint for a patient with other diseases that cause a characteristic change of the musculoskeletal joint over time.

Although specific embodiments of the invention have been described above, it will be appreciated that various modifications can be made to the described embodiments without departing from the spirit and scope of the present invention. That is, the described embodiments are to be considered in all respects exemplary and non-limiting. In particular, where a particular form has been described for particular processing, it will be appreciated that such processing may be carried out in any suitable form arranged to provide suitable output data.

The invention claimed is:

1. A computer-implemented method for generating anatomical data of a musculoskeletal joint of interest of a patient, the method comprising:
receiving as input variation data representing change with time of a musculoskeletal joint of interest caused by a musculoskeletal joint disease, wherein the variation data comprises a vector containing values of variation with time of a shape of the musculoskeletal joint of interest caused by the musculoskeletal joint disease from an initial time to a subsequent time, the initial time being a time at which the musculoskeletal joint of interest is less affected by disease as compared to the subsequent time, and wherein the variation data models variation with time of a training set of data of individuals other than the patient;
receiving as input patient data, the patient data representing the musculoskeletal joint of interest of the patient at a first time, wherein the patient data representing the musculoskeletal joint of interest of the patient comprises a representation of a shape of the musculoskeletal joint of interest of the patient, wherein the representation of the shape of the musculoskeletal joint of interest of the patient is based upon a parameterisation of the musculoskeletal joint of interest;
processing the variation data and the patient data to generate said anatomical data, wherein said anatomical data comprises data of the musculoskeletal joint of interest of the patient at a second time prior to the first time to indicate effects of the musculoskeletal joint disease, wherein processing the variation data and the patient data to generate said anatomical data comprises varying the shape represented by the patient data based upon the variation data, and wherein varying the shape represented by the patient data based upon the variation data comprises applying the vector to the parameterisation;
generating, and displaying on a display device, a three-dimensional model of the musculoskeletal joint of interest of the patient at the second time based on the anatomical data; and
manufacturing, via three-dimensional printing, a customized prosthesis based on the musculoskeletal joint of interest of the patient with the effects of the musculoskeletal joint disease removed.

2. The method of claim 1, wherein the musculoskeletal joint disease is osteoarthritis.

3. The method of claim 1, further comprising generating the patient data by:
receiving image data obtained from the patient; and
processing the image data to generate the parameterisation.

4. The method of claim 1, wherein the representation of the shape of the musculoskeletal joint of interest of the patient comprises a plurality of principal components of the shape of the musculoskeletal joint of interest of the patient.

5. The method of claim 1, wherein applying the vector to the parameterisation comprises:
determining a relationship between the patient data and an average shape; and
varying the shape represented by the patient data based upon the determined relationship.

6. The method of claim 1, wherein the musculoskeletal joint of interest is a hip joint or a knee joint.

7. The method of claim 1, wherein the anatomical data comprises a representation of the musculoskeletal joint of interest of the patient with reduced effects of the musculoskeletal joint disease.

8. The method of claim 1, further comprising generating said variation data.

9. The method of claim 8, wherein generating said variation data comprises:
determining an average change with time of a plurality of musculoskeletal joints of interest.

10. The method of claim 1, wherein said anatomical data comprises data suitable for providing a medical intervention for the musculoskeletal joint of interest of the patient.

* * * * *